United States Patent [19]

Sachse

[11] Patent Number: 5,391,155
[45] Date of Patent: Feb. 21, 1995

[54] ARRANGEMENT COMPRISING A URETER TUBE, AN AUXILIARY TUBE AS WELL AS A MANDRIN

[76] Inventor: Hans Sachse, Lerchenstrasse 55, 8500 Nürnberg, Germany

[21] Appl. No.: 942,891

[22] Filed: Sep. 11, 1992

[30] Foreign Application Priority Data

Sep. 13, 1991 [DE] Germany ............ 4130433.0
Dec. 13, 1991 [DE] Germany ............ 4141154.4

[51] Int. Cl.$^6$ .................................... A61M 5/178
[52] U.S. Cl. ........................... 604/170; 604/164; 604/264; 604/280
[58] Field of Search ............ 604/27, 43, 48, 164, 604/170, 264, 280

[56] References Cited

U.S. PATENT DOCUMENTS

| | | | |
|---|---|---|---|
| 3,890,977 | 6/1975 | Wilson | 128/418 |
| 4,212,304 | 7/1980 | Finney | 128/349 |
| 4,787,884 | 11/1988 | Goldberg | 604/170 |
| 4,790,331 | 12/1988 | Okada et al. | 128/772 |
| 4,804,365 | 2/1989 | Litzie et al. | 604/280 |
| 4,834,702 | 5/1989 | Rocco | 604/170 |
| 4,950,257 | 8/1990 | Hibbs et al. | 604/264 |
| 4,969,875 | 11/1990 | Ichikawa | 604/170 |
| 5,083,572 | 1/1992 | Pokorny | 604/27 |
| 5,183,470 | 2/1993 | Wettermann | 604/170 |

FOREIGN PATENT DOCUMENTS

| | | |
|---|---|---|
| 3824244 | 1/1990 | Germany . |
| 3921634 | 1/1990 | Germany . |
| 3900738 | 7/1990 | Germany . |
| 9015815.6 | 4/1991 | Germany . |

*Primary Examiner*—John G. Weiss
*Attorney, Agent, or Firm*—Keil & Weinkauf

[57] ABSTRACT

A device for the insertion of a ureter into the ureter or renal pelvis has a ureter tube with an opening of its distal tip, an auxiliary tube and a mandrin. In the insertion position, at least the ureter tube and mandrin are releasably connected. A connecting-piece at the proximal end of the mandrin makes an injection of an X-ray contrast medium into the hollow space inside the mandrin possible where it passes to an outlet opening at the distal end of the mandrin which outlet opening has an entry to the ureter. The mandrin preferably has an inherent curvature in its distal tip and a moveable steering wire can be placed into the lumen of the mandrin.

5 Claims, 5 Drawing Sheets

ARRANGEMENT COMPRISING A URETER TUBE, AN AUXILIARY TUBE AS WELL AS A MANDRIN

BACKGROUND OF THE INVENTION

1. Field of the Invention

[The starting point of the present invention is represented by an arrangement according to the preamble of claim 1. Such an arrangement is described in U.S. Pat. No. 4,212,304.] The invention relates to an arrangement for the insertion of a ureter tube into the ureter or renal pelvis comprising a ureter tube, an auxiliary tube and a movable mandrin.

2. Description of the Related Art

An arrangement comprising a ureter tube, an auxiliary tube and a mandrin is described in U.S. Pat. No. 4,212,304.

With such an arrangement, it is possible to insert the ureter tube into the ureter with the aid of a massive mandrin. After removal of the massive mandrin the arrangement remains in the ureter because of an inherent curvature in the form of a hook at both ends (also called "memory") at the renal pelvis and the inner wall of the bladder. However, the introduction of an X-ray contrast [media] medium into the ureter was not possible. The necessary X-ray contrast media had to be introduced first into the ureter by separate measures before the ureter tube could be introduced. Such a procedure of introducing an arrangement twice is time-consuming for the physician and troublesome for the patient.

It is an object of this invention to improve the arrangement as described in U.S. Pat. No. 4,212,304 in such a way that the introduction of an X-ray contrast [media] medium can be carried out faster and simpler for the patient and by requiring less actions by the physician.

[It has been found that starting with the arrangement according to the preamble of claim 1, such an object can be achieved by using] It has been found that such an improved arrangement for the insertion of a ureter tube into the ureter or renal pelvis comprising a ureter tube, an auxiliary tube and a mandrin, each having an upper or distal and a lower or proximal end and a mandrin, which mandrin is movable in longitudinal direction relative to the ureter tube and the auxiliary tube, and the auxiliary tube and the ureter tube are slidable over the mandrin, can be achieved if the mandrin of the arrangement is a hollow mandrin, in which the cross-section of the hollow space inside of the mandrin is open for the injection of an X-ray medium, the hollow space inside of the mandrin has in the section of its upper (distal) tip at least one outlet opening for the passage of an X-ray contrast medium which outlet opening has an entry to the ureter, and if the hollow space inside of the mandrin has at its other (proximal) end, projecting from the auxiliary tube, a connecting-piece or opening for the introduction of the X-ray contrast medium, and if the ureter tube has a front-side opening at its upper (distal) tip. In the arrangement, it is of advantage to use a hollow single mandrin, i.e. a mandrin with a hollow space inside of it. The cross-section of the hollow space inside of the mandrin is, throughout its length, [always] open for the injection of X-ray contrast media, and has in the area of its upper (distal) tip or end at least one opening or outlet for the passage of X-ray contrast media. The opening - preferably by a front-face opening of the tip of the ureter tube - has an entry to the ureter. The hollow space inside of the mandrin has, at its other (proximal) end, [a connection or opening for introducing an X-ray contrast media (claim 1) projecting over the auxiliary tube.] projecting over the auxiliary tube, a connecting-piece or opening for introducing an X-ray contrast medium. The hollow space inside the mandrin provides a sufficiently large through hole for the passage of an X-ray contrast media. A physician can permanently introduce an X-ray contrast media into the ureter during the insertion of the ureter tube, auxiliary tube and the single hollow mandrin which stiffens the ureter tube. The position of the ureter tube and in particular of its distal tip can be controlled via X-ray radioscopy during the insertion procedure. The advantages for both the physician and the patient are the shortening of the insertion procedure as well as a lower number of manipulations that are endured by the patient.

A [proximal] distal opening of the tip of the ureter tube is described in the German Utility Model 9,0 15,815. This [proximal] distal opening is described only in connection with, inter alia, a double mandrin. [The present invention, on the other hand, concerns a single mandrin as claimed in claim 1.]

[Furthermore, the invention starts from an arrangement as given in the preamble of claim 2 which is particularly suitable for the insertion of the ureter tube and its execution by the physician. Such an arrangement is described with a double mandrin in German Utility Model 90 15,815.] In an embodiment of the described arrangement, it is possible to inject X-ray contrast [media] medium through the inner hollow-cylindrical cavity of the outer mandrin and the central opening at the [face] front-side of the upper (distal) tip of the ureter tube into the ureter, after pulling out the inner mandrin, whereby an X-ray contrast [media] medium can reach the renal pelvis.

Here and in the following description, the term upper tip of the ureter tube shall refer to the [proximal] distal end of the ureter tube which is inserted into the ureter. The term tip of the mandrin resp. inner mandrin shall refer to the [proximal] distal end of the mandrin resp. inner mandrin which is directed toward the patient.

Though the [described] arrangement described in German Utility Model 90 15 815 represented an essential improvement of the then existing prior art, e.g. as described in U.S. Pat. No. 4,212,304, it had a disadvantage in that the physician has to pull out the inner mandrin from the ureter tube respectively the outer mandrin first before an X-ray contrast [media] medium could be introduced, and then has to reinsert the inner mandrin again into the outer mandrin in order to stiffen and to straighten the inherent curvature of the tip of the ureter tube. These are two time-wasting steps for the physician which risks the danger of an undesired migration of the position of the ureter tube, as well as incurring unpleasant and time-consuming manipulations for the patient.

As alternative embodiment, German Utility Model 9,015,815 discloses enlarging the lumen, i.e. the cylindrical space between the inner mandrin and the outer mandrin, to such a degree, that when the inner mandrin is not pulled out, the X-ray contrast [media] medium can be introduced via the enlarged lumen and via the central side opening of the tip of the ureter tube into the ureter or into the renal pelvis. This alternative embodiment, however, has a disadvantage in that the production costs of such equipment increases due to the necessity of a reproducible and reliable precision of manufacturing a lumen of such dimensions. A further disadvantage is that there is not much room, with respect to the cross-section difference, for the lumen to allow the flow of an X-ray contrast media. Hence, the X-ray contrast media must be injected with very high pressure. This is so because the outer diameter of the ureter tube must not exceed a certain size.

[According to the preamble of claim 2,] In one embodiment of an arrangement according to this invention a double mandrin with an outer mandrin and a hollow inner mandrin can be used. The inner mandrin is movable in longitudinal direction relative to the outer mandrin and the ureter tube and auxiliary tube are slidable over the double mandrin. The hollow space inside of the inner mandrin has in the section of its upper (distal) tip at least one upper outlet opening for the passage of X-ray contrast medium and at its other (proximal) end a connecting-piece or opening for the introduction of the contrast medium. The outlet openings have an entry tg the ureter which can be direct or via the front-side or front-face opening of the upper (distal) tip of the ureter tube. In one embodiment of this invention the upper (distal) outlet opening (23;9) of the mandrin (21) or inner mandrin (4) is formed by the upper (distal) tip (22;4b) of the mandrin and is in the insertion position flush to or slightly below the front-side opening (11) of the upper (distal) tip of the ureter tube. Mandrin and inner mandrin of the arrangement are preferably a metal tube or plastic tube. In a preferred arrangement of this invention, the ureter tube and mandrin resp. outer mandrin are in a configuration for insertion in that they are releasably but firmly connected. They can be clamped together in the (proximal) end section of the [auxiliary] ureter tube. The term "insertion position" [in the preamble of claim 2] shall mean the configuration of the ureter tube, mandrin and auxiliary tube relative to each other during the insertion of the total arrangement into the ureter and also during the introduction of an X-ray contrast media. Such a releasable connection between the mandrin resp. outer mandrin and ureter tube is described in the German Patent Application DE-OS 3,900,738 filed by the Applicant. After additional use of a clamping connection for the mandrin resp. outer mandrin at the (proximal) end section of the auxiliary tube, the ureter tube, the mandrin resp. double mandrin and the auxiliary tube form a functional unit. For facilitating the insertion the functional unit allows forward, backward and rotational movements of the ureter tube and of the curvatures of the tip of the ureter tube and allows after proper positioning of the ureter tube an easy removal of the mandrin and auxiliary tube. The disclosure of German Patent Application DE-OS 3,900,738 is incorporated herewith by reference, in particular with respect to the therein described different possibilities for a releasable connection between ureter tube and mandrin resp. outer mandrin like the clamping by means of a thickening of the mandrin resp. outer mandrin which increase the diameter (there claims 4, 5 and 6 and FIGS. 2, 3 and 4), or of the ureter tube (there claims 1 and 2 and FIG. 1) or by using an insert between the mandrin resp. outer mandrin and the ureter tube (there claim 8 and FIGS. 7 and 8) in such a way that when setting the arrangement in the insertion configuration, the ureter tube and the mandrin resp. outer mandrin are connected by clamping. The clamping or friction between mandrin resp. outer mandrin and ureter tube can be released by pulling the mandrin resp. outer mandrin in a longitudinal direction while at the same time the auxiliary tube avoids movement of the ureter tube. The mentioned friction can be increased by roughening the surfaces or providing them with grooves. A releasable connection between mandrin resp. outer mandrin and ureter tube is also possible by the use of a releasable screwing as described in the German Patent Application DE-OS 3,824,244 the disclosure whereof is also incorporated herewith by reference. The releasable screwing gives a functional unit of the two parts allowing said rotational, forward and backward movements of the arrangement.

It is a further object to improve the [arrangement of the preamble of claim 2] known arrangements for the insertion of a ureter tube in such a way that more functions are given to the mandrin, in particular to use it for a simpler and less expensive introduction of X-ray contrast media.

These further objects can be achieved by an arrangement [according to claim 2] comprising ureter tube, auxiliary tube and mandrin like a double mandrin and having the above described characteristics of the arrangement according to this invention. The cylindrical hollow-space inside of the inner mandrin resp. mandrin forms a passage for an X-ray contrast medium from the inlet opening of the mandrin, positioned outside of the body, to the ureter. This results in some advantages. The cylindrical hollow-space inside of the inner mandrin resp. mandrin has a relatively large cross-section and thereby enables the fast passage of a sufficient amount of X-ray contrast medium to the ureter respectively to the renal pelvis under relatively low pressures. There is no need to pull out the inner mandrin from the ureter tube for the transport of an X-ray contrast medium to the ureter, the inner mandrin can stay in its insertion position. Hence, the surgeon saves valuable time. Furthermore, in a preferred embodiment, it is possible to move the arrangement of ureter tube, mandrin and auxiliary tube and to bring the tip of the ureter tube into the final position in the renal pelvis during the introduction of an X-ray contrast media to the ureter. If necessary, there is also the possibility to move the inner mandrin resp. mandrin relative to the ureter tube. By pulling back the inner mandrin resp. mandrin, the inherent curvature of the tip of the ureter tube will be no more straightened, thereby allowing the curvature of the tip of the ureter tube to adapt, if necessary, to the curvature of the ureter. Other advantage are very important for the physician because the ureter and the renal pelvis can be examined and the ureter tube can simultaneously be moved. This is especially important for the proper positioning of the curved tip of the ureter tube within the renal pelvis.

[The preferred embodiment of the invention given in claim 3 allows] In a preferred embodiment of this invention where the upper (distal) outlet opening (23,9) of the mandrin (21) or inner mandrin (4) is formed by the distal tip (22;4b) of the mandrin (21) or inner mandrin (4) and where in the insertion position the opening is flush to or slightly below the front-side opening (11) of the upper (distal) tip (12) of the ureter tube, the hollow-space (10) of the ureter tube forms a passage of the X-ray contrast medium from the outlet opening (23;9) of the tip (22) of the mandrin or of the tip of the inner mandrin (4b) to the opening (11) of the tip (12) of the ureter tube. Such arrangement allows an optimal straight-line flow of an X-ray contrast medium from the inlet of the medium to the ureter.

[An alternative embodiment of the invention, according to claims 4, 5 and 6, show further possibilities of the position of the upper outlet opening or openings.]

[The embodiment of the invention according to claim 7 offers the further] In another embodiment of the invention the inner mandrin (4) or mandrin (21) projects above the front-side opening of the upper (distal) tip of the ureter tube in the insertion position and has in such upper (distal) end of the mandrin or inner mandrin an inherent curvature or memory. Such arrangement has a steering wire (18) in the hollow-space (8) inside of the inner mandrin (4) or mandrin (21) which is essentially stiff against bending and movable in the longitudinal direction. Preferably the upper (distal) tip of the inner mandrin can be closed against passage of the steering wire and against passage of the X-ray contrast medium. It is an advantage to provide also the upper section of the inner mandrin resp. mandrin with an inherent curvature, sometimes also called "memory". Such an inherent curvature is in particular known for the tip of the ureter tube where the curvature can be straightened by use of the mandrin during the insertion of the ureter tube. After having reached the final position, in which the upper tip of the ureter tube is in the renal pelvis and its lower tip is in the bladder, the mandrin is pulled out. The tips of the ureter tube then take the shape of its inherent curvature which keep themselves at the inner wall of the bladder or in the renal pelvis thereby avoiding migration. A similar inherent curvature in the tip area of the mandrin, which essentially surpasses the tip of the ureter tube, is possible too. Here it is an advantage that a special steering wire of the inner mandrin resp. mandrin compensates the inherent curvature and thus effects a straightening of the tip of the inner mandrin resp. mandrin. Such tip of the inner mandrin resp. mandrin which surpasses the tip of the ureter tube can have a variable inherent curvature and can easily bypass obstructions, pass narrow passages and follow twisty courses of the ureter and make its way to the renal pelvis much easier than the thicker tip of the ureter tube. The ureter tube being thicker than the inner mandrin resp. mandrin can then follow the prepared way.

Further advantages and characteristics of the present invention can be seen in or easily derived from [the claims, from] the following description and from the drawings relating thereto.

DESCRIPTION OF THE PREFERRED EMBODIMENTS

Figure 1:
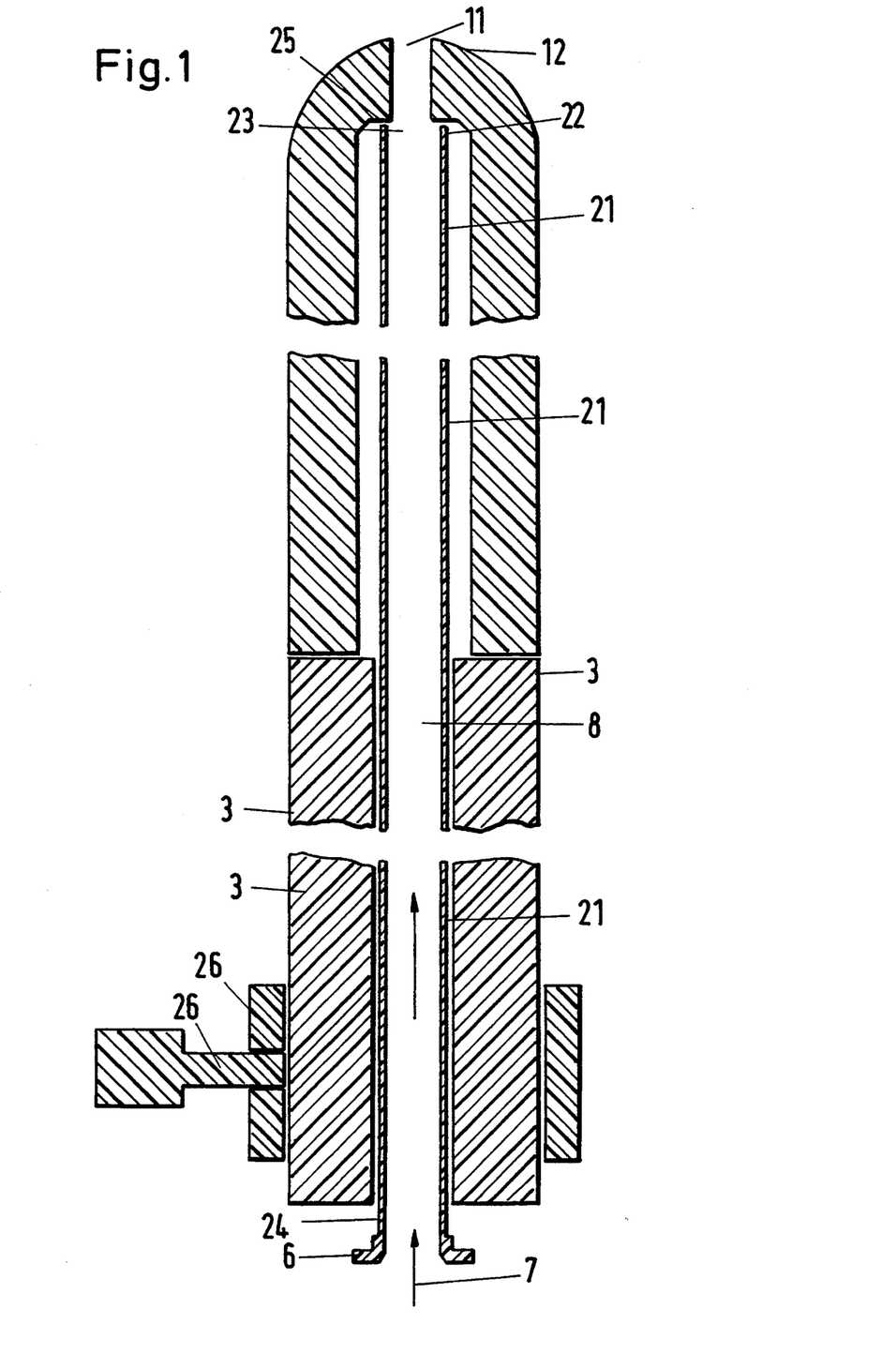
FIG. 1 shows a first embodiment of the invention in longitudinal section.

FIG. 1 shows a simplified embodiment of the invention consisting of a ureter tube (1) having an outlet opening (11) at its upper tip. The ureter tube (1) is hollow and contains a hollow-cylindrical single mandrin (21). Its tip (22) has an outlet opening (23). The hollow-cylindrical single mandrin (21) is arranged with an auxiliary tube (3) from which its lower end (24) projects. There is a connecting-piece (6) for an injection pump or other suitable equipment for injecting an X-ray contrast media in the direction of arrow 7 into the hollow space inside of the single mandrin (21). From there the medium passes through the openings (23) and (11) into the ureter, provided that the tip (12) of the ureter tube is already in the ureter.

The upper tip (22) of the single mandrin (21) strikes against a projection or edge (25) within the upper tip (12) of the ureter tube. Thus a slipping out or projection of the single mandrin (21) through the upper opening (11) can be avoided. Regarding it in the introduction direction of an X-ray contrast medium, the opening (23) of the single mandrin (21) is before the opening (11) of the ureter tube. FIG. 1 shows inside of the single mandrin (21) a steadily free continuous hollow space extending from the injection according to arrow 7 down below up to opening (23). Auxiliary tube (3) and single mandrin (21) can be connected in the lower area of the auxiliary tube by a releasable clamping device (26), e.g. a clamp bolt.

Figure 2:
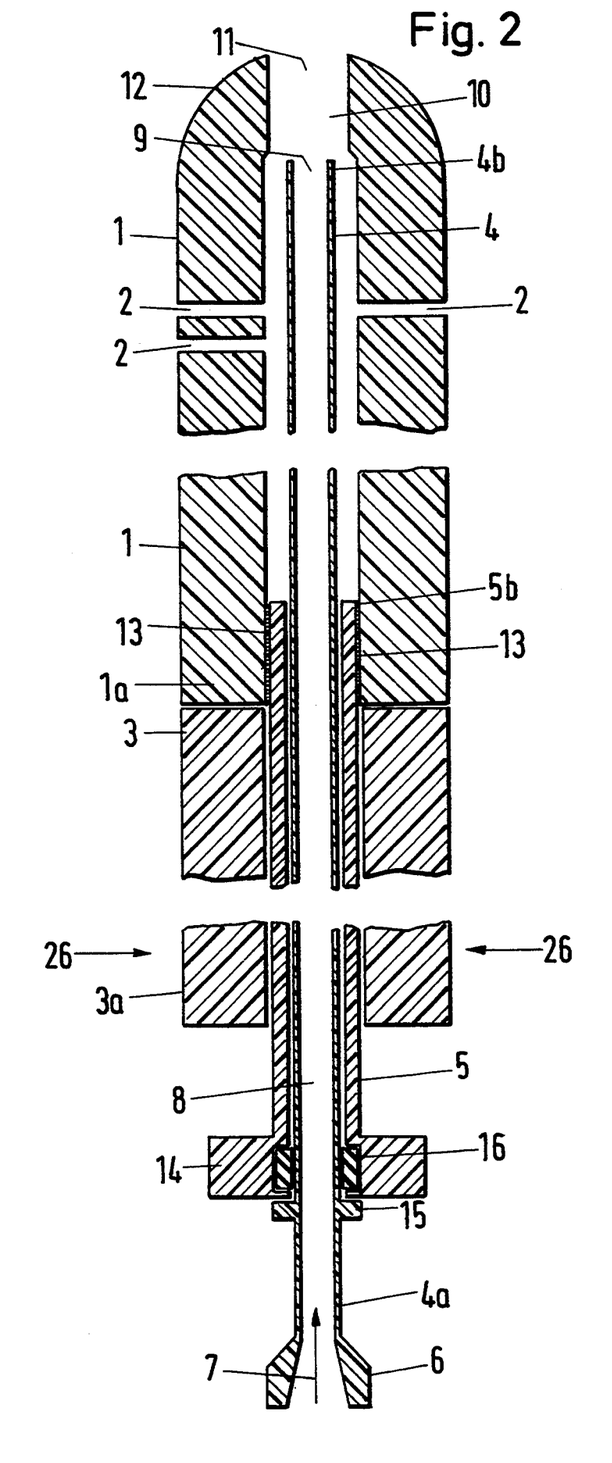
FIG. 2 shows a second embodiment of the invention in longitudinal section.

The arrangement according to FIG. 2 essentially consists of a ureter tube (1) having drainage channels (2), an auxiliary tube (3) and a double mandrin. The mandrin consists of the inner mandrin (4) and the outer mandrin (5). Both are long cylinders. The inner mandrin (4) preferably consists of an elastic metal tube or plastic tube. In this embodiment of the invention the lower end (4a) of the inner mandrin is also provided with a connecting-piece for a syringe (not shown) to inject an X-ray contrast medium into the inner mandrin in the direction of arrow 7. The X-ray contrast medium flows through the cylindrical hollow space (8) inside of the inner mandrin and through a front-side opening (9) at the upper end or tip (4b) of the inner mandrin upwards and then through a cylindrical inside cavity (10) and a front side outlet opening (11) of the tip (12) of the ureter tube into the ureter. The lower part (1a) of the ureter tube and the upper part (5b) of the outer mandrin are clamped together, e.g. by a longitudinal thickening or sleeve (13). After having finished the insertion of the ureter tube into the ureter, the outer mandrin can be removed by pulling it downward at its handle (14) overcoming the clamping forces between the parts (1a), (13) and (5b). The auxiliary tube (3) avoids pulling of the ureter tube (1). After having pulled out the outer mandrin, the auxiliary tube (3) can be removed from the bladder and urethra. Such a procedure is known by itself. In case of a clamping of the outer mandrin with the ureter tube, the inner mandrin (4), if necessary, can be removed from the outer mandrin by pulling in the direction opposite to the direction of arrow 7. For the insertion of the arrangement auxiliary tube (3), the outer mandrin (5) and inner mandrin (4) are clamped together by a releasable clamping device, e.g. a clamp bolt or clamping tape, preferably at the lower part (3a) of the auxiliary tube. [In FIG. 2 the clamping is only schematically indicated by the double arrows (26).] With such clamping the positioning of the insertion position is achievable as hereinafter described.

The upper tip (4b) of the inner mandrin is either flush with the central opening (11) of the tip (12) of the ureter tube or positioned close to the tip (12). Thus the tip (4b) does not touch the ureter. After insertion of the tip (12) of the ureter tube into the ureter, an X-ray contrast medium is introduced into the ureter in the described manner whereby the ureter becomes visible in the radiograph. The injection of the X-ray contrast medium can be steadily repeated during the pushing-upward of the ureter tube whereas the X-ray contrast media shows a certain lubricating effect and facilitates the pushing-upward of the ureter tube. While pushing the ureter tube upward, the auxiliary tube (3), the outer mandrin (5) and the inner mandrin (4) are clamped together by means of the mentioned screw or a similar clamping device (26) catching hold at the lower end of the auxiliary tube (3). Simultaneously, clamping (13) between the outer mandrin and the ureter tube is achieved. In order to avoid a projection of tip (4b) of the inner mandrin over the outlet opening (11) of the tip of the ureter tube, a safety ring (15) can be provided at the lower part (4a) of the inner mandrin which will push against the handle (14) of the outer mandrin (5) when the upper final position of the inner mandrin has been reached. A gasket (16) avoids leakage of the X-ray contrast media. Furthermore there can be a [screening] screwing of the inner mandrin to the outer mandrin.

Figure 3:
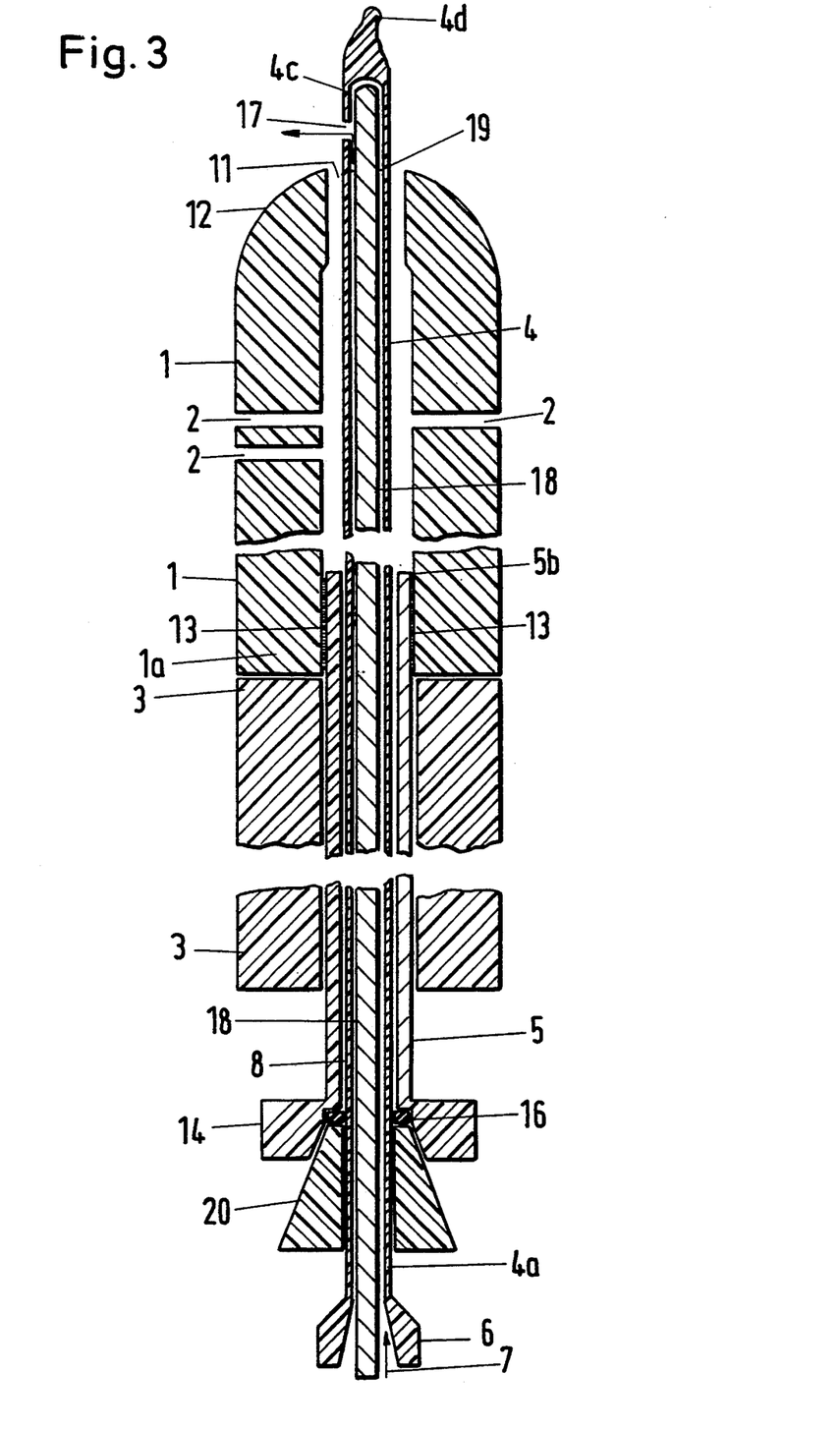
FIG. 3 shows a third embodiment of the invention in longitudinal section.

In the drawing of the embodiment of the invention corresponding to FIG. 3, all parts similar to parts shown in FIG. 2 have the same numbers. The embodiment shown in FIG. 3 mainly differs from that shown in FIG. 2 by a change of the upper end section (4c) of the inner mandrin which has at least one lateral outlet opening for the X-ray contrast medium. Furthermore there is a steering wire (18) in the hollow space (8) inside of the inner mandrin (4). The upper end section (4c) of the inner mandrin has a tip (4d) which is preferably closed. Thus there is no outlet of the X-ray contrast medium and no projection of the upper end of the steering wire (18). The upper end section (4c) of the inner mandrin has an inherent curvature formed and provided by the manufacturer. [This is indicated in the drawing by a dot-dash line and number (4e).] In order to have formed such curvature, the steering wire (18) has to be pulled down so far that its upper front end is located at or below position (19). As the upper end section (4c) of the inner mandrin is closed at its tip (4d), there are provided one or more lateral openings (17) in the wall of the inner mandrin for the outlet of the X-ray contrast media. This inner mandrin can be from the beginning mounted in such a way that its tip projects by a certain length, e.g. 7 mm, over the tip (12) of the ureter tube (1). It can be stiffened by the steering wire (18). That inner mandrin (4), but also the mandrin (21) according to the embodiments of the invention shown in FIGS. 4 and 5, can be made so long that it sufficiently, e.g. 5 cm, projects from the tip of the ureter tube and simultaneously the inner mandrin or mandrin projects on the side of the physician so much that it can be grasped as a handle. But the inner mandrin (4) and the mandrin (21) can with its upper end section and its tip (4d,22) totally pulled into the tip (12) of the ureter tube. In cases where the ureter has extreme narrow passages and/or the course of the ureter is full of corners, such an inner mandrin serves to find and pave the way for the thicker tip (12) of the ureter tube. For such purposes, it can be advantageous to change the position of the inner mandrin (4) in length direction of the ureter tube relative to the position of the outer mandrin (5) (and thus also relative to the ureter tube) and to fix it in the desired position with a releasable clamping device, preferably in the lower part of the auxiliary tube as indicated in FIG. 1 and FIG. 2 by number (26). In principle, such clamping between inner mandrin and outer mandrin could also be provided at another position. This applies in particular for the extent of the projection of the tip of the inner mandrin past the tip of the ureter tube. The tip can be centrically or eccentrically arranged in relation to the outer mandrin. Its steering function described below is very essential for finding the right track through the ureter up to the renal pelvis. For certain manipulations it can be advantageous to releasably clamp together the inner mandrin (4) or the mandrin (21, FIG. 1) with the steering wire (18), e.g. by means of a releasable clamping device as schematically indicated in FIG. 3 by number (20).

In the above-mentioned use of the inner mandrin for finding and paving a way through extreme narrow passages or through a course of the ureter full of corners, it can be advantageous, if the tip of the inner mandrin has the mentioned inherent curvature which can extend from the tip (4d) to the position (19). Thus the treating physician is provided with an arrangement consisting of a thin inner mandrin and a thicker ureter tube where the tips of both have an inherent curvature. Depending on the shape and course of the ureter, the physician can, having regarded the X-ray photograph, decide if he stiffens and straightens the tip of the inner mandrin by the steering wire or uses said tip in its curved pigtail shape for finding the way, or if he pulls back the inner mandrin into the ureter tube and finds the way to the renal pelvis by use of the tip of the ureter tube only. The pig-tail curvatures of both inherent curvatures, i.e. of the tips of the inner mandrin and of the ureter tube, can have opposite directions or, preferably, the same direction what can be reached e.g. by oval cross-section shapes. If the steering wire (18) is used, its removal before the injection of the X-ray contrast media according to arrow 7 is recommended.

Figure 4:
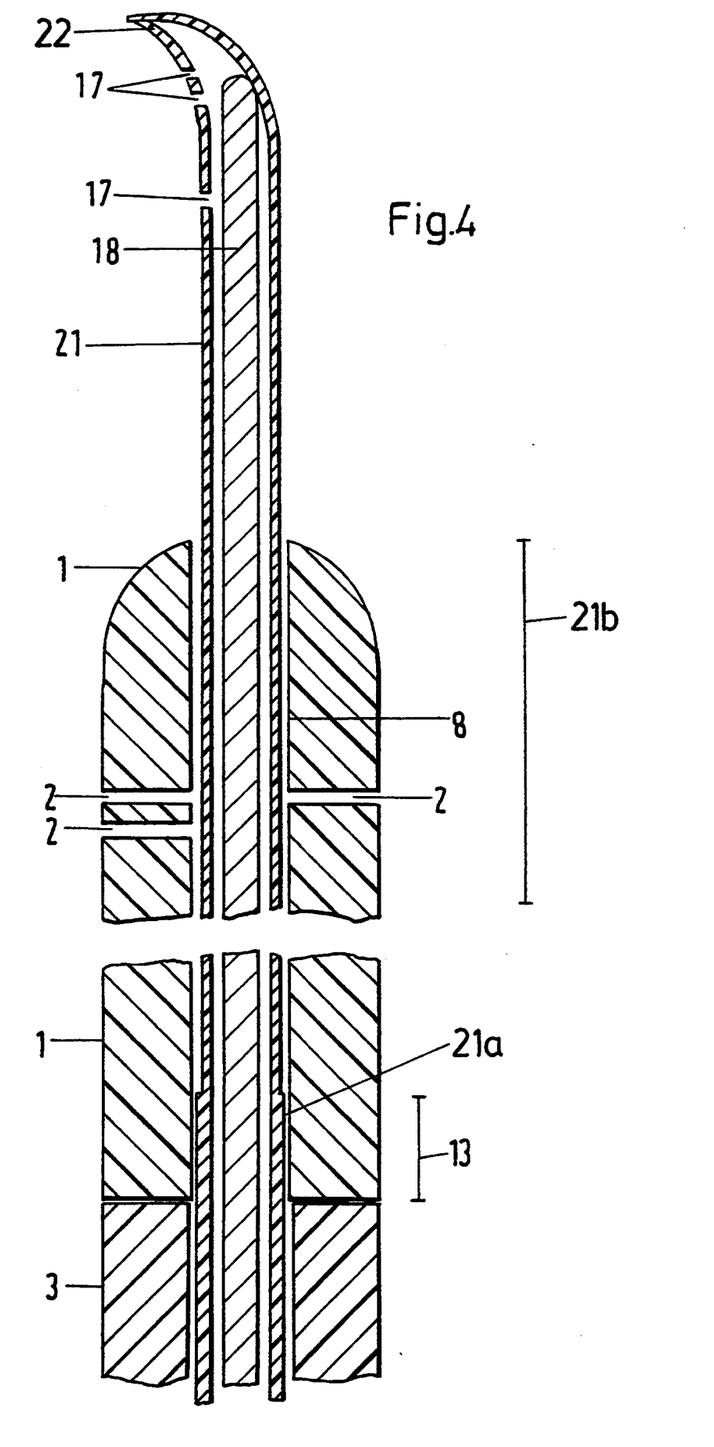
FIG. 4 and FIG. 5 show the upper and lower part of a further embodiment of the invention in longitudinal section.
Figure 5:
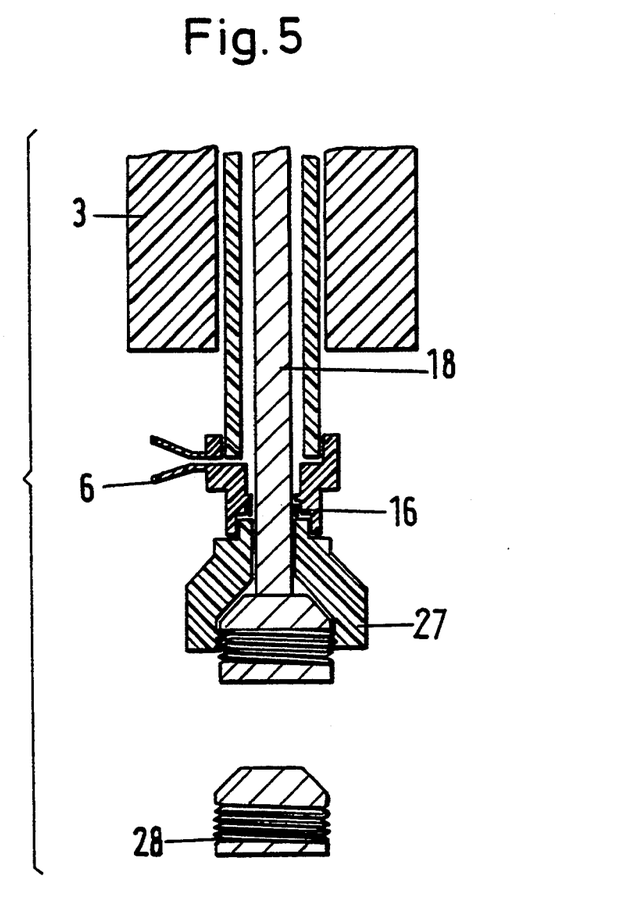

The embodiment according to FIGS. 4 and 5 follow that of FIG. 1 in so far as only a hollow mandrin (21) is provided for the passage of the X-ray contrast medium. The upper section of the mandrin has outlet openings (17) and an inherent curvature similar to the upper section of the embodiment according to FIG. 3 and includes a steering wire (18). With respect to the outlet openings of the ureter tube etc. the same numbers as for FIG. 3 are used. (21b) is the upper part of the mandrin (21) and corresponds to (5b) in FIG. 3. The mandrin (21) has in the lower section of the auxiliary tube a thickening (increase in diameter) [(21')] (21a) which - as indicated by number (13) - is clampable with the inner wall (8) of the ureter tube. There is a cylindric hollow-space between the inner wall of the mandrin and the steering wire (18) allowing to transport X-ray contrast medium via the openings (17) into the ureter. The auxiliary tube (3) is loosely slid onto the outer wall of the thickening (increased diameter position) [(21')] (21a). The connecting-piece [(6')] (6) serves for affixing an injection syringe of the X-ray contrast medium. A handle [(22)] (27) is screwed onto the lower section of the steering wire (18). After screwing off the handle, the steering wire (18) can be pulled out from the mandrin what facilitates the introduction of the X-ray contrast media into the ureter. Therefor the locking screw [(24)] (28) has to be screwed together with the handle [(22)] (27) in order to avoid a downward outflow of the X-ray contrast media.

Features described for one of the embodiments of the invention can be used also in connection with other embodiments of the invention to the extent technically feasible.

I claim:

1. An arrangement for the insertion of a ureter tube into the ureter or renal pelvis comprising a ureter tube, an auxiliary tube and a mandrin, each having a distal and a proximal end, said mandrin being movable in longitudinal direction relative to the ureter tube and the auxiliary tube and the ureter tube are slidable over the mandrin, wherein, the mandrin is a hollow single mandrin (21) encompassing a hollow space (8) inside of the mandrin whose cross-section is open for injection of an X-ray contrast medium, the hollow space (8) inside of the mandrin (21) has near its distal tip (22) at least one outlet opening for the passage of an X-ray contrast medium which outlet opening has an entry to the ureter, the hollow-space (8) inside of the mandrin (21) has at its proximal end (24), projecting from the auxiliary tube (3), a connecting-piece (6) for the introduction of the X-ray contrast medium, and the ureter tube (1) has a front-side opening of its distal tip (12).

2. An arrangement for the insertion of a ureter tube into the ureter or the renal pelvis as defined in claim 1, wherein the outlet opening for the passage of the X-ray contrast medium has an entry to the ureter via a front-side opening of the distal tip (12) of the ureter tube.

3. An arrangement for the insertion of a ureter tube into the ureter or renal pelvis as defined in claim 1, wherein in the insertion position the mandrin (21) projects above the front-side opening of the distal tip of the ureter tube (1) and has in such distal tip of the mandrin (22) an inherent curvature, and has in the hollow space (8) inside of the mandrin (21), a steering wire (18) being essentially stiff against bending and being movable therein in the longitudinal direction.

4. An arrangement for the insertion of a ureter tube into the ureter or renal pelvis as defined in claim 1, wherein the mandrin (21) has in the section of its distal tip (22) at least one lateral outlet opening (17).

5. An arrangement for the insertion of a ureter tube into the ureter or renal pelvis as defined in claim 4, wherein in the insertion position of the arrangement the lateral outlet opening (17) of the distal end (22) of the mandrin (21) is outside of the distal tip of the ureter tube.

* * * * *